US00PP31021P2

(12) United States Plant Patent
Heimovaara

(10) Patent No.: US PP31,021 P2
(45) Date of Patent: Nov. 5, 2019

(54) ***CHRYSANTHEMUM* PLANT NAMED 'ZANMUMADORE YELLOW'**

(50) Latin Name: ***Chrysanthemum* x *morifolium* Ramat.**
Varietal Denomination: Zanmumadore Yellow

(71) Applicant: Van Zanten Breeding BV, Aalsmeer (NL)

(72) Inventor: Sjoukje Heimovaara, Valkenburg (NL)

(73) Assignee: VAN ZANTEN BREEDING BV (NL)

( * ) Notice: Subject to any disclaimer, the term of this patent is extended or adjusted under 35 U.S.C. 154(b) by 0 days.

(21) Appl. No.: 16/350,059

(22) Filed: Sep. 21, 2018

(51) Int. Cl.
*A01H 5/02* (2018.01)
*A01H 6/14* (2018.01)

(52) U.S. Cl.
USPC ..... Plt./289
CPC ..... *A01H 6/14* (2018.05); *A01H 5/02* (2013.01)

(58) Field of Classification Search
USPC ..... Plt./289
CPC ..... A01H 5/0255
See application file for complete search history.

*Primary Examiner* — Kent L Bell
(74) *Attorney, Agent, or Firm* — Steptoe & Johnson LLP

(57) ABSTRACT

A *chrysanthemum* plant named 'Zanmumadore Yellow' characterized by its medium sized blooms with yellow ray florets and dark centers and prolific branching; natural season flowering date October 2 (week 41); blooming for a period of 5 weeks.

3 Drawing Sheets

Botanical designation: *Chrysanthemum* x *morifolium* Ramat.

Cultivar denomination: 'Zanmumadore Yellow'.

RELATED CULTIVARS

The new plant is a flower color mutant of 'Zanmumadore' (unpatented)

BACKGROUND OF THE INVENTION

The present invention relates to a new and distinct cultivar of *chrysanthemum* plant, botanically known as *Chrysanthemum* x *morifolium* Ramat, commercially known as a garden mum, and hereinafter referred to by the cultivar denomination 'Zanmumadore Yellow'. 'Zanmumadore Yellow' is a product of a breeding and selection program which had the objective of finding flower color mutants from existing parent plants. The new plant comprises a whole plant mutant of the parent *chrysanthemum* named 'Zanmumadore' (unpatented). Plants from the new cultivar 'Zanmumadore Yellow' differ from plants of the parent in the color of the ray-florets. The ray-florets of the parent are pink, while those of the new plant are yellow.

In order to obtain color mutants, unrooted cuttings of the parent plant were irradiated in April 2014 at Ziekenhuis, Rotterdam, the Netherlands, with gamma radiation at a dose of 15Gy. These treated cuttings were then planted in a controlled environment (greenhouse) in Rijsenhout, the Netherlands. In this population of planted cuttings, the new cultivar was discovered as a natural flower color mutant in October 2014 by Sjoukje Heimovaara. The first act of asexual reproduction of 'Zanmumadore Yellow' was accomplished when after planting of the 'Zanmumadore Yellow' as a motherplant in December 2014, vegetative cuttings from this 'Zanmumadore Yellow' were taken and propagated further in Rijsenhout, the Netherlands. In summer, about 6-8 days are needed to initiate roots in cuttings of the new cultivar, after another 5 days rooted plants are formed. The new cultivar has been found to retain its distinctive characteristics through successive asexual propagations.

BRIEF DESCRIPTION OF THE DRAWINGS

The present invention of a new and distinct variety of *chrysanthemum* (of about 22 weeks) is shown in the accompanying drawings, the color being as nearly true as possible with color photographs of this type.

DESCRIPTION OF THE INVENTION

Figure 1:
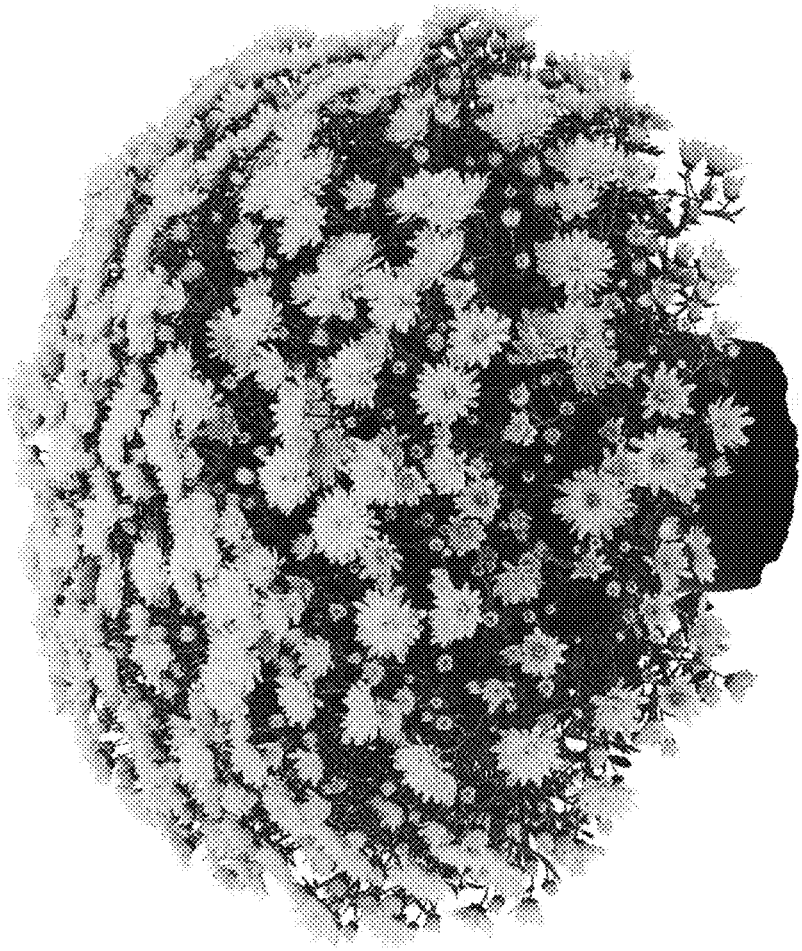
FIG. 1 shows a plant of the cultivar in full bloom.
Figure 2:
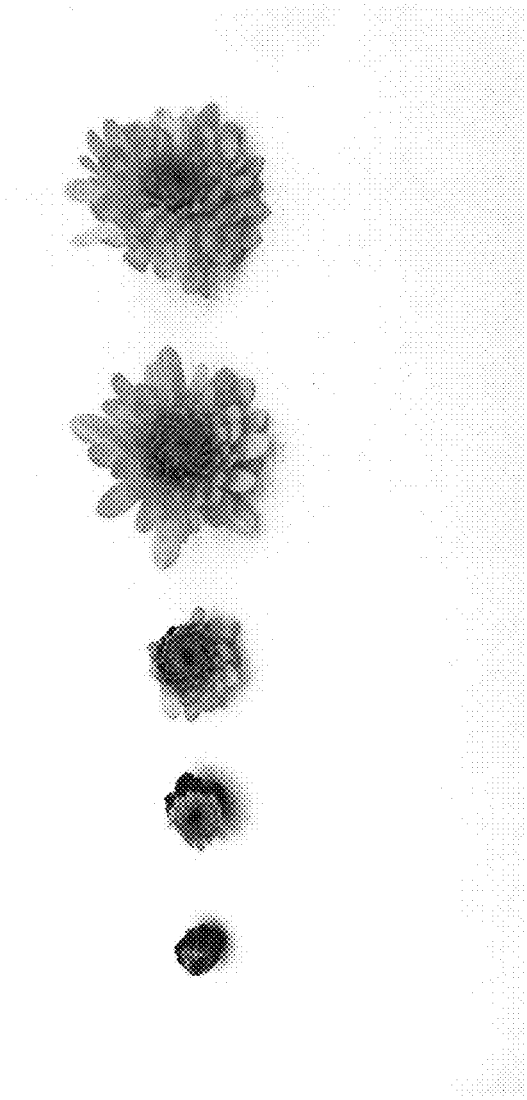
FIG. 2 shows the various stages of blooms of the new cultivar.
Figure 3:
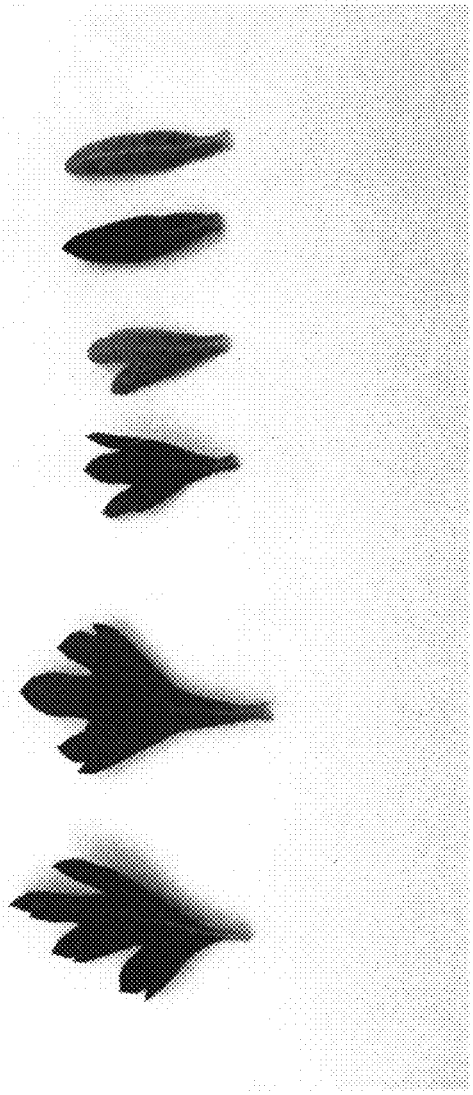
FIG. 3 shows the various stages of foliage of the new cultivar.

The observations and measurements were gathered from plants in the period of 19 to 25 weeks of age grown outdoors in Rijsenhout, the Netherlands, under natural day length and temperature and planted in week 22 in 2017. The natural blooming date of this crop was October 2 (week 41). The average height of the plants was 25-30 cm. No growth retardants were used. No tests were done on disease or insects resistance or susceptibility. No tests were done on cold or drought resistance. This new variety produces medium sized blooms with yellow ray florets and a dark center blooming for a period of five weeks.

From the cultivars known to the inventor the most similar existing cultivars in comparison to 'Zanmumadore Yellow' is its parent 'Zanmumadore' and 'Zanmumadore Orange'. When 'Zanmumadore', 'Zanmumadore Yellow' and 'Zanmumadore Orange' are being compared the following differences are noticed: ray floret color in 'Zanmumadore' is pink, yellow in 'Zanmumadore Yellow' and bronze in 'Zanmumadore Orange'.

The following is a description of the plant and characteristics that distinguish 'Zanmumadore Yellow' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, sixth edition, 2015.

TABLE 1

Botanical Description of *Chrysanthemum* × *morifolium* Ramat. 'Zanmumadore Yellow'

| | |
|---|---|
| Bud | |
| Size: | Small; cross-section 5 mm, height 4 mm |
| Shape: | Round |
| Texture: | Pubescent |
| Outside color: | Greyed-green 191A |
| Phyllaries | |
| Number: | 24, arranged in 3 rows |
| Shape: | Elliptic |
| Apex: | Acute |
| Base: | Truncate |
| Margin: | Entire |
| Color: | Upper side: Green 139A<br>Lower side: Green N138C |
| Length and width: | 0.6-0.8 mm; 2-4 mm |
| Texture: | Pubescent |
| Inflorescences | |
| Type: | Double |
| Height: | 13 cm |
| Diameter: | 3.5-4 cm |
| Peduncle length: | 6-7 cm |
| Peduncle color: | Green 138B |
| Peduncle diameter: | 1.5 mm |
| Peduncle texture: | Pubescent |
| Peduncle strength: | Medium |
| Number per branch: | About 8-9 inflorescences |
| Duration of flowering: | 5 weeks |
| Seeds: | Produced in small quantities, ovate, Greyed-brown 199A, length 1.5 mm, diameter 0.5 mm; texture: rough with ribs |
| Fragrance: | Faint *chrysanthemum* odor |
| Color inflorescences | |
| Center of inflorescence: | Immature stage: Yellow 13A;<br>Mature stage: Yellow 13A |
| Color of upper side of ray florets (outer rows): | Yellow 12B |
| Color of lower side of ray florets (outer rows): | Yellow-orange 17B |
| Color of upper side ray florets (inner rows): | Yellow 10A |
| Color of lower side ray-florets (inner rows): | Yellow-orange 17B |
| Tonality from distance: | A garden mum with bronze blooms and a dark center |
| Color of ray florets after aging of the plant: | Yellow 10A |
| Ray florets | |
| Number of types: | 2 |
| Type: | Ligulate |
| Rows: | about 15 |
| Texture: | Upper and lower side smooth |
| Number: | outer rows: 140; inner rows: 30 |
| Shape: | outer rows: elliptic; inner rows: narrowly elliptic |

TABLE 1-continued

Botanical Description of *Chrysanthemum* × *morifolium* Ramat. 'Zanmumadore Yellow'

| | |
|---|---|
| Apex: | outer rows: dentate; inner rows: dentate |
| Base: | attenuate |
| Cross-section: | outer rows: flat; inner rows: concave |
| Longitudinal axis: | outer rows: straight; inner rows: straight |
| Length of corolla tube: | 3 mm |
| Diameter | corolla tube: 1 mm |
| Ray floret margin: | Entire |
| Ray floret length (outer rows): | 1.5-2 cm |
| Ray-floret length (inner rows): | 0.8-1 cm |
| Ray-floret width (outer rows): | 3 mm |
| Ray | floret width (inner rows): 1 mm |
| Ratio length/width: | Medium |
| Disc | florets Absent |
| Receptacle | |
| Color: | Yellow-green 145D |
| Shape: | Domed raiscd |
| Height: | 3-4 mm |
| Diameter: | 4 mm |
| Reproductive Organs | |
| Androecium: | Absent |
| Pollen: | Lacking |
| Gynoecium: | Present on ray florets |
| Style color: | Yellow-green 154C |
| Style length: | 4 mm |
| Stigma color: | Yellow 7A |
| Stigma width: | 1 mm |
| Ovary: | Enclosed in calyx |
| Ovary color: | Yellow-green 149D |
| Plant | |
| Type: | Bushy |
| Growth habit: | Spherical shape |
| Growth rate: | High |
| Height: | 25-30 cm |
| Width: | 40-45 cm |
| Stem color: | Greyed-brown 199A |
| Stem strength: | Not strong |
| Stem brittleness: | Brittle |
| Stem anthocyanin coloration: | absent |
| Internode length: | 0.5-2.5 cm |
| Length of lateral branch: | From top to bottom 20-22 cm |
| Lateral branch color: | Green 137 C |
| Lateral branch, attachment: | Weak |
| Lateral branch diameter: | 3 mm |
| Lateral branch texture: | pubescent with ribs |
| Branching (average number of lateral branches): | Medium with 8 breaks after pinching |
| Natural season blooming date: | October 2 (week 41) in Rijsenhout, the Netherlands. |
| Root habits: | Fine, freely branching |
| Root color: | White155D |
| Rooting time: | 6-8 days |
| Formation rooted plants: | 12-14 days |
| Foliage | |
| Leaf glossiness: | Upper side: very weak<br>Lower side: absent |
| Leaf color: | Upper side: Green 136A<br>Lower side: Green 137A. |
| Color mid vein: | Upper side: Yellow-green 147D<br>Lower side: Yellow-green 148D |
| Size: | Small; length 2.5-5 cm, width 0.8-2 cm |
| Quantity (number per lateral branches): | about 25 |
| Shape: | Elliptic to obovate |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |

TABLE 1-continued

| Botanical Description of *Chrysanthemum* × *morifolium* Ramat. 'Zanmumadore Yellow' | |
|---|---|
| Margin of sinus between lateral lobes: | Diverging |
| Shape of base: | Acute |
| Apex: | Mucronulate |
| Petiole attitude: | Moderately upwards |
| Petiole length: | 0.1-0.8 cm |
| Petiole diameter: | 3 mm |
| Petiole color: | Yellow-green 147D |
| Stipules: | present, small |

TABLE 2

| Differences with the comparison variety, when grown under identical conditions | | | |
|---|---|---|---|
| | 'Zanmumadore' | 'Zanmumadore Yellow' | 'Zanmumadore Orange' |
| Color upper side ray floret-outer row | Red-purple 72C | Yellow 12B | Greyed-orange 163C |
| Color upper side ray floret color-inner row | Red-purple 72A | Yellow 10A | Greyed-red 178A |

I claim:

1. A new and distinct *chrysanthemum* plant named 'Zanmumadore Yellow' as described and illustrated.

* * * * *